(12) United States Patent
Haeberlin

(10) Patent No.: US 6,887,459 B1
(45) Date of Patent: May 3, 2005

(54) AEROSOL COMPOSITION COMPRISING FORMOTEROL

(75) Inventor: Barbara Haeberlin, Muenchenstein (CH)

(73) Assignee: Novartis, AG, Basel (CH)

( * ) Notice: Subject to any disclaimer, the term of this patent is extended or adjusted under 35 U.S.C. 154(b) by 0 days.

(21) Appl. No.: 10/148,043

(22) PCT Filed: Nov. 28, 2000

(86) PCT No.: PCT/EP00/11894

§ 371 (c)(1),
(2), (4) Date: May 24, 2002

(87) PCT Pub. No.: WO01/39745

PCT Pub. Date: Jun. 7, 2001

(30) Foreign Application Priority Data

Nov. 30, 1999 (GB) ............................................. 9928311

(51) Int. Cl.⁷ .............................. A61K 9/12; A61K 9/14
(52) U.S. Cl. ........................... 424/45; 424/46; 424/489; 424/443; 424/435; 514/826
(58) Field of Search ............................ 424/45, 46, 489, 424/443, 435, 450, 404; 514/826, 78, 554, 360, 653; 128/200.14, 200.21, 203.15

(56) References Cited

U.S. PATENT DOCUMENTS 5,795,564 A * 8/1998 Aberg et al. ................... 424/45
6,045,828 A * 4/2000 Bystrom et al. ............ 424/489

FOREIGN PATENT DOCUMENTS

| WO | WO 93/11773 A | 6/1993 |
| WO | WO 98/31351 A | 7/1998 |
| WO | WO 99/15182 A | 4/1999 |
| WO | WO 00/47200 A | 8/2000 |

OTHER PUBLICATIONS

Maesen FPV et al., "Formoterol as dry Powder Inhalation", Chest, Park Ridge, Il, US vol. 101, No. 5, 1992, pp. 1376–1381, XP000911155.

Barnes, P J: "Chronic obstructive pulmonary disease: new opportunities for drug development", Trends in Phamacological Sciences, Elsevier Trends Journal, Cambridge, GB, vol. 19, No. 10, Oct. 1998, pp. 415–423.

Maesen B L P et al., "Effects of formoterol in apparently poorly reversible chronic obstructive pulmonary disease", European Respiratory Journal, vol. 13, No. 5, May 1999, pp. 1103–1108, XP001020413, ISSN: 0903–1936 the whole document.

Sichletidis et al., Int. J. Clin. Pract., vol. 53, No. 3., pp. 185–188, "Bronchodilatory Responses to Formoterol, Ipratropium, and Their Combination in Patients with Stable COPD" (1999).

British National Formulatory, British Medical Association & Royal Pharmaceutical Society, September, No. 38, see Section 3.1.3, pp. 131–132 (1999).

Reynolds (ed), "Martindale. The Extra Pharmacopoeia", 31st edition, Royal Pharmaceutical Society, p. 1575 (re. eformoterol fumarate), p. 1567 (re. chronic obstructive pulmonary disease) and pp. 1591–1593 (re.salbutamol), 1996.

* cited by examiner

Primary Examiner—Michael G. Hartley
Assistant Examiner—Mina Haghighatian
(74) Attorney, Agent, or Firm—Gregory C. Houghton

(57) ABSTRACT

The use of a dry powder comprising (A) formoterol, or a pharmaceutically acceptable salt or solvate thereof, or solvate of said salt, and (B) a pharmaceutically acceptable particulate diluent or carrier in an amount of from 400 μg to 5000 μg per μg of (A) for the preparation of an inhalable medicament for the treatment of chronic obstructive pulmonary disease.

10 Claims, No Drawings

AEROSOL COMPOSITION COMPRISING FORMOTEROL

This invention relates to the use of organic compounds in the treatment of chronic obstructive pulmonary disease (COPD), both reversible and irreversible COPD, reversibility being defined by reference to the effect of inhalation of a standard dose of a short-acting beta-2 agonist bronchodilator such as salbutamol on the forced expiratory volume in 1 second ($FEV_1$) measured by spirometry. The characteristics of different stages of COPD are described in the Official Satement of the American Thoracic Society (ATS): Am J Respir Crit Care Med Vol 152, pp 577–120, 1995, and a Consensus Statement of the European Respiratory society (ERS): European Respiratory Journal 1995, 8, 1398–1420.

It has now surprisingly been found, in accordance with the invention, that formoterol or a pharmaceutically acceptable salt or solvate thereof or solvate of said salt, each hereinafter alternatively referred to as the formoterol active ingredient, is particularly effective in the treatment of COPD when administered by inhalation as a dry powder in admixture with a diluent or carrier in an amount of from 400 μg to 5,000 μg per μg of formoterol active ingredient. Administration of such a mixture by inhalation to COPD patients facilitates significant sustained bronchodilation, a very good safety profile, important e.g. for the treatment of COPD without significant concomitant cardiovascular effects, and significant improvement in Quality of Life as assessed by the St George's Respiratory Questionnaire (SGRQ).

Accordingly, the present invention provides, in one aspect, the use of a dry powder comprising (A) formoterol, or a pharmaceutically acceptable salt or solvate thereof, or solvate of said salt, and (B) a pharmaceutically acceptable particulate diluent or carrier in an amount of from 400 μg to 5,000 μg per μg of (A) in the preparation of an inhalable medicament for the treatment of chronic obstructive pulmonary disease.

In a related aspect, the present invention provides a pharmaceutical composition in the form of a dry powder comprising (A) and (B) as hereinbefore defined for use in the treatment of chronic obstructive pulmonary disease.

In another aspect, the present invention provides a method of treating chronic obstructive pulmonary disease which comprises administering by inhalation to a subject in need of such treatment an effective amount of a dry powder comprising (A) formoterol, said formoterol being in free form or in the form of a pharmaceutically acceptable salt or solvate thereof or in the form of a solvate of such a salt, and (B) a pharmaceutically acceptable particulate diluent or carrier in an amount of from 400 μg to 5,0000 μg per μg of (A).

In a further aspect, the present invention provides the use of a dry powder comprising (A) formoterol, or a pharmaceutically acceptable salt or solvate thereof, or solvate of said salt, and (B) a pharmaceutically acceptable particulate diluent or carrier in an amount of from 400 μg to 5,000 μg per μg of (A), said dry powder being substantially free from fluticasone proprionate, mometasone furoate or tiotropium salts, for the preparation of an inhalable medicament for the treatment of chronic obstructive pulmonary disease.

The formoterol active ingredient (A) may be in any isomeric form or mixture of isomeric forms, for example a pure enantiomer, particularly the R,R-enantiomer, a mixture of enantiomers, a racemate or a mixture thereof. Pharmaceutically acceptable salts of formoterol include acid addition salts with inorganic acids such as hydrochloric acid, hydrobromic acid, sulphuric acid or phosphoric acid, or organic acids such as acetic, succinic, glutaric, maleic, fumaric, citric, tartaric, lactic, benzoic, salicylic, p-hydroxybenzoic, p-methoxybenzoic, hydroxynapthoic, methanesulfonic, benzesulfonic, or p-toluenesulfonic acid. Suitable solvates of formoterol and pharmaceutically acceptable salts thereof include hydrates. A preferred form of formoterol for use in accordance with the invention is formoterol fumarate, especially formoterol fumarate dihydrate, conveniently in racemic form. Formoterol, salts and hydrates thereof and salt hydrates thereof as hereinbefore described may be prepared by known methods, for example as described in U.S. Pat. No. 3,994,974 or U.S. Pat. No. 5,684,199.

Accordingly, in a preferred embodiment, the present invention provides the use of a dry powder consisting, or consisting essentially, of (A) formoterol fumarate dihydrate and (B) a pharmaceutically acceptable diluent or carrier in an amount of from 400 μg to 5,000 μg per μg of (A) for the preparation of an inhalable medicament for the treatment of chronic obstructive pulmonary disease.

Suitable diluents or carriers include saccharides and/or sugar alcohols, e.g. monosaccharides, disaccharides and polysaccharides such as glucose, arabinose, dextrose, fructose, ribose, mannose, sucrose, trehalose, lactose, maltose or dextran, sugar alcohols such as mannitol and mixtures of two or more thereof. A preferred diluent or carrier is lactose, particularly in the form of the monohydrate. The diluent or carrier is generally present in an amount of 400 to 4000 μg, for example 800 to 3000 μg, more preferably 1000 to 2500 μg, especially 2000 to 2500 μg, per μg of formoterol active ingredient (A). The mean particle diameter of the formoterol active ingredient (A) is preferably up to 10 μm, more preferably up to 5 μm, especially 1 to 5 μm. The diluent or carrier (B) may be present in the dry powder in the form of particles having, for example, a maximum diameter of 300 μm, a preferred maximum being 212 μm. The diluent or carrier (B) may conveniently have a median particle diameter of 40 to 100 μm, e.g. 50 to 75 μm. The particle size of the formoterol active ingredient (A), and that of the diluent or carrier (B), can be reduced to the desired level by conventional methods, for example by grinding in an air-jet mill, ball mill or vibrator mill, by sieving, by microprecipitation, by spray-drying, by lyophilisation or by recrystallisation from supercritical media.

In a preferred embodiment of the invention, the dry powder is in a capsule, usually of a pharmaceutically acceptable natural or synthetic polymer such as gelatin or hydroxypropyl methylcellulose, the capsule containing a unit dose of formoterol active ingredient (A). Doses of formoterol active ingredient (A) to be inhaled in accordance with the invention may be, in general, from 1 μg to 60 μg. When (A) is formoterol fumarate dihydrate, the dose may be, for example, from 6 μg to 48 μg. Preferred doses are from 6 μg to 36 μg, for example 6 μg, 12 μg, 18 μg, 24 μg, 30 μg, or 36 μg, the 12 μg and 24 μg being especially preferred and the 12 μg dose the most preferred. These doses may be administered once or twice daily, preferably twice daily, the preferred maximum daily dose being 48 μg. For on demand usage, the 6 μg or 12 μg dose is preferred, being inhaled as needed in accordance with a preferred maximum daily dose of 48 μg. When the dry powder is in a capsule containing a unit dose of (A), e.g. 6 μg, 12 μg or 24 μg of (A), the amount of diluent/carrier is preferably such as to bring the total weight of dry powder per capsule to between 5 mg and 25 mg, e.g. to 5 mg, 10 mg, 15 mg, 20 mg or, especially, 25 mg.

In especially preferred embodiements the dry powder is in a capsule, the capsule containing 12 μg of formoterol active ingredient (A) and 4988 μg to 49988 μg, for example 4988 μg or 9988 μg or 14988 μg, more preferably 19988 μg to 24988 μg, for example 19988 μg or, especially, 24988 μg of diluent or carrier (B).

As will be understood by those skilled in the art, a dry powder contained in a capsule may be inhaled by inserting the capsule in a dry powder inhalation device adapted to pierce a capsule containing the dry powder on actuating the device, thereby releasing the dry powder for inhalation by the user—a dry powder capsule inhaler. Such devices are well known in the art and are commercially available. For example, a suitable inhalation device is described in U.S. Pat. No. 3,991,761, which is incorporated herein by reference, particularly as described in the claims of U.S. Pat. No. 3,991,761 and as described with reference to the drawings of U.S. Pat. No. 3,991,761; this device may be modified by coating the capsule-piercing pins with a polymer, as described in WO99/45987. A preferred inhalation device is one adapted to receive a single capsule containing the dry powder, i.e. a single capsule inhaler, for example the commercially available Aerolizer® inhaler.

In another preferred embodiment of the invention, the dry powder may be in a reservoir of a multi-dose dry powder inhaler adapted to deliver a unit dose, for example 5 μg, 6 μg, 9 μg, 10 μg, 12 μg, 15 μg, 18 μg, 20 μg, 24 μg, 25 μg, 30 μg or 36 μg, preferably from 5 to 15 μg of formoterol active ingredient (A), particularly formoterol fumarate dihydrate, per actuation, for example from a powder having a formoterol fumarate dihydrate:lactose weight ratio of 5:4995, 5:9995, 5:14995, 10:4990, 10:9990, 10:14990, 12:4988, 12:9988 12:14998, 15:9985 or 15:14985. Multi-dose dry powder inhalers are well known in the art and are commercially available. For example, a suitable multi-dose inhaler is that described in WO97/20589.

Treatment of COPD in accordance with the invention includes treatment of reversible or irreversible, mild, moderate or severe COPD (including chronic bronchitis and emphysema) and conditions associated therewith, e.g. bronchospasm, loss of lung function, loss of exercise capacity, breathlessness, dyspnea or loss of lung elasticity. Thus treatment of COPD in accordance with the invention includes maintenance (prophylactic) treatment or on-demand or rescue treatment of bronchospasm associated with COPD, treatment to slow progressive loss of lung function, treatment to improve exercise capacity, and treatment to improve Quality to Life according to the SGRQ.

The effect of compositions of the invention in the treatment of COPD can be monitored in a conventional manner, e.g. by determining parameters such as forced expiratory volume in 1 second ($FEV_1$), vital capacity (VC), forced vital capacity (FVC), Quality of Life, peak expiratory flow (PEF), exercise capacity (e.g. Shuttle Walking Test) and lung compliance (CL) at intervals during treatment. Quality of Life may be measured according to the SGRQ (P. W. Jones et al., Respir Med. 1991; 85 (Suppl B): 25–31).

The invention is illustrated by the following Examples.

EXAMPLE 1

Gelatin capsules suitable for use in a capsule inhaler are prepared, each capsule containing a dry powder consisting of 6 μg of formoterol fumarate dihydrate which has been ground to a mean particle diameter of 1–5 μm in an air jet mill and 4994 μg of lactose monohydrate having a particle diameter of below 212 μm. These capsules are used in the treatment of COPD patients by inserting a capsule into the capsule chamber of the inhaler described in U.S. Pat. No. 3,991,761 and actuating the piercing devices to perforate the capsule and release the dry powder when air is inhaled through the capsule chamber by a patient.

EXAMPLES 2–29

Example 1 is repeated using the amounts of the formoterol fumarate dihydrate and the lactose monohydrate shown in the table below in place of the amounts used in that Example:

| Example | Formoterol Fumarate Dihydrate (μg) | Lactose Monohydrate (μg) |
|---|---|---|
| 2 | 6 | 9994 |
| 3 | 6 | 14994 |
| 4 | 6 | 19994 |
| 5 | 6 | 24994 |
| 6 | 12 | 4988 |
| 7 | 12 | 9988 |
| 8 | 12 | 14988 |
| 9 | 12 | 19988 |
| 10 | 12 | 24988 |
| 11 | 12 | 29988 |
| 12 | 18 | 9982 |
| 13 | 18 | 14982 |
| 14 | 18 | 19982 |
| 15 | 18 | 24982 |
| 16 | 18 | 29982 |
| 17 | 24 | 9976 |
| 18 | 24 | 14976 |
| 19 | 24 | 19976 |
| 20 | 24 | 24976 |
| 21 | 24 | 29976 |
| 22 | 30 | 14970 |
| 23 | 30 | 19970 |
| 24 | 30 | 24970 |
| 25 | 30 | 29970 |
| 26 | 36 | 14964 |
| 27 | 36 | 19964 |
| 28 | 36 | 24964 |
| 29 | 36 | 29964 |

EXAMPLE 30

Two groups of patients suffering from COPD are treated with formoterol. One group has reversible COPD, showing at least 15% increase in $FEV_1$ 30 minutes after inhaling 200 μg of salbutamol. The other group has irreversible COPD, showing less than 15% increase in $FEV_1$ 30 minutes after inhaling 200 μg of salbutamol. Both groups are treated by inhalation twice daily for 12 weeks from a capsule containing a dry powder consisting of 12 μg of formoterol fumarate dihydrate having a mean particle diameter of 1 to 5 μm and 24988 μg of lactose monohydrate having a particle diameter below 212 μm, using an Aerolizer® inhaler. After treatment for 12 weeks, the patients' lung function ($FEV_1$) is measured at intervals for 12 hours after dosing, the measured $FEV_1$ is plotted against time after dosing and the area under the curve (AUC) of the resulting plot is determined.

What is claimed is:

1. A method of treating chronic obstructive pulmonary disease consisting essentially of administering by inhalation to a subject in need of such treatment an effective amount of a dry powder comprising (A) formoterol, or a pharmaceutically acceptable salt or solvate thereof, or solvate or said salt, and (B) a pharmaceutically acceptable particulate diluent or carrier in an amount of 400 μg to 5,000 μg per μg of (A), wherein said pharmaceutically acceptable diluent or carrier has a median particle diameter of 40 to 100 μm, and said formoterol is the only active ingredient.

2. A method according to claim 1, in which the formoterol (A) is in the form of formoterol fumarate dihydrate.

3. A method of treating chronic obstructive pulmonary disease which comprises administering by inhalation to a subject in need of such treatment an effective amount of a dry powder consisting, or consisting essentially, of (A) formoterol fumarate dihydrate and (B) a pharmaceutically acceptable diluent or carrier in an amount from 400 $\mu$g to 5,000 $\mu$g per $\mu$g of (A), wherein said pharmaceutically acceptable diluent or carrier has a median particle diameter of 40 to 100 $\mu$m.

4. A method according to claim 3, in which the diluent or carrier (B) is a saccharide, a sugar alcohol or a mixture thereof.

5. A method according to claim 4, in which the diluent or carrier (B) is lactose.

6. A method according to claim 3, in which the diluent or carrier (B) is present in an amount of 800 to 3000 $\mu$g per $\mu$g of (A).

7. A method according to claim 3, in which the mean particle diameter of (A) is up to 10 $\mu$m.

8. A method according to claim 3, in which the dry powder is in a capsule, the capsule containing a unit dose of (A).

9. A method according to claim 8, in which the capsule contains 12 $\mu$g of (A) and 19988–24988 $\mu$g of diluent or carrier (B).

10. A method according to claim 3, in which the dry powder is in a reservoir of a multi-dose powder inhaler adapted to deliver a unit dose of (A) per actuation.

\* \* \* \* \*